United States Patent [19]

Dockner

[11] Patent Number: 4,727,193

[45] Date of Patent: Feb. 23, 1988

[54] REDUCTION OF TERITIARY PHOSPHINE OXIDES, PHOSPHINE SULFIDES OR PHOSPHINE DIHALIDES WITH HYDROCARBONS

[75] Inventor: Toni Dockner, Meckenheim, Fed. Rep. of Germany

[73] Assignee: BASF Aktiengesellschaft, Ludwigshafen, Fed. Rep. of Germany

[21] Appl. No.: 875,197

[22] Filed: Jun. 17, 1986

[30] Foreign Application Priority Data

Jun. 29, 1985 [DE] Fed. Rep. of Germany ....... 3523320

[51] Int. Cl.$^4$ ............................................. C07F 9/50
[52] U.S. Cl. ........................................ 568/8; 568/12
[58] Field of Search ....................................... 568/8, 17

[56] References Cited

U.S. PATENT DOCUMENTS

| | | | |
|---|---|---|---|
| 3,031,509 | 4/1962 | Marshall et al. | 568/8 |
| 3,261,871 | 7/1966 | Fritzsche et al. | 568/8 X |
| 3,280,195 | 10/1966 | Fritzsche et al. | 568/17 |
| 3,405,180 | 10/1968 | Natoli | 568/17 X |
| 3,481,988 | 12/1969 | Wünsch et al. | 568/17 |
| 3,775,482 | 11/1973 | Hewertson et al. | 568/17 X |
| 3,780,111 | 12/1973 | Young et al. | 568/8 X |
| 3,855,311 | 12/1974 | Staendeke | 568/8 |
| 4,008,282 | 2/1977 | Townsend et al. | 568/17 |
| 4,113,783 | 5/1978 | Malpass et al. | |
| 4,246,204 | 1/1981 | Broger | 568/17 |
| 4,249,023 | 2/1981 | Broger | 568/17 |
| 4,301,301 | 11/1981 | Fukui et al. | 568/17 |

FOREIGN PATENT DOCUMENTS 2516361 10/1976 Fed. Rep. of Germany .

OTHER PUBLICATIONS

Houben–Weyl, Methoden der Org. Chemie, vol. 12/1, pp. 58, 61, 129 and 168 (1962).

*Primary Examiner*—Helen M. S. Sneed
*Attorney, Agent, or Firm*—John H. Shurtleff

[57] ABSTRACT

Tertiary phosphine oxides, phosphine sulfides and/or phosphine dihalides are reduced to tertiary phosphines by reaction with a hydrocarbon in the presence of carbon at elevated temperatures.

18 Claims, No Drawings

REDUCTION OF TERTIARY PHOSPHINE OXIDES, PHOSPHINE SULFIDES OR PHOSPHINE DIHALIDES WITH HYDROCARBONS

The present invention relates to a process for the reduction of tertiary phosphine oxides, phosphine sulfides and/or phosphine dihalides to tertiary phosphines.

Tertiary phosphine oxides are among the most stable compounds of phosphorus and are extremely resistant to reducing agents. Catalytic hydrogenation and reduction with elemental metals are not possible. For example, tributylphosphine oxide is transferred to dibutyl phosphine only in molten sodium at 300°–360° C., an alkyl radical being lost at the same time. Aromatic phosphine oxides react with alkali metals to form colored products which are similar to the metal ketyls and which are converted to alkali metal salts of phosphinous acid at elevated temperatures. If it is desired to reduce tertiary phosphine oxides, it is therefore advisable first to convert them to phosphine dihalides or phosphine sulfides by reacting them with, for example, phosphorus pentachloride, thionyl chloride or sulfur tetrafluoride, and, if required, to react the dihalides obtainable in this manner further with hydrogen sulfide to give the phosphine sulfides. Both intermediates can be converted to the tertiary phosphines, for example with elemental metals (Houben-Weyl,, Methoden der Org. Chemie, Vol. 12/1, pages 58, 129 and 168, 1962).

Direct reduction to tertiary phosphines can be carried out only with complex hydrides, for example lithium aluminum hydride (loc. cit., page 61) at elevated temperatures. In this procedure, there if a tendency for an aryl radical to be eliminated from aromatic phosphine oxides, so that secondary phosphines are formed as a by-product. Triphenylphosphine oxide can be converted to triphenylphosphine according to U.S. Pat. No. 4,113,783 and by reaction with dialkylaluminum hydride followed by basic hydrolysis.

The formation of tertiary phosphine oxides, in particular triphenylphosphine oxide, plays a role in, for example, the Wittig reaction (Merck Index, 10th edition, 1983, ONR-96) for the synthesis of olefins by reaction of carbonyl compounds with alkylenetriphenylphosphoranes (ylides) (also see Ullmann's Enzylkopädie d. techn. Chemie, 4th edition, Vol. 18, pages 382 and 383, 1979). Although this reaction is of great preparative value, large amounts of triphenylphosphine oxide are produced and have to be converted to the phosphines by involved methods, for example via the phosphine dihalides, or have to be disposed of.

It is an object of the present invention to provide a process which makes it possible for tertiary phosphine oxides, or the dihalides or phosphine sulfides obtainable from them, to be converted to the tertiary phosphine in a cheap manner and on an industrial scale.

We have found, suprisingly, that this object is achieved by a simple process for the reduction of tertiary phosphine oxides, phosphine sulfides and/or phosphine dihalides to tertiary phosphines, wherein an organic phosphorus compound of the general formula I

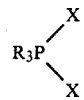

where each radical X is halogen or the two radicals X together represent an oxo or thio group and R is an aliphatic, cycloaliphatic, araliphatic or aromatic radical, is heated with a hydrocarbon in the presence of carbon.

The process according to the invention is represented, for example, by the equations below.

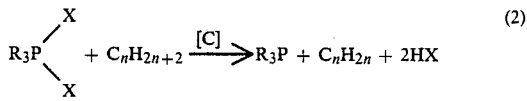

X=halogen.

The hydrogen required for the formation of $H_2O$ or HX is derived from the hydrocarbon, which produces, as end products, not only derivatives having a lower hydrogen content but frequently also carbon.

Suitable radicals R are aliphatic, cycloaliphatic, araliphatic and aromatic radicals, for example alkyl radicals such as methyl, ethyl, n-propyl, isopropyl, n- and isobutyl, pentyl, octyl and higher alkyl radicals which may furthermore contain double or triple bonds, as well as cycloalkyl radicals, in particular those of 5 to 6 carbon atoms, such as cyclohexyl, and aralkyl, alkylaryl, aralkenyl and aralkynyl, e.g. benzyl or phenyl ethyl. Triaryl-substituted phosphorus compounds, e.g. triphenylphosphine oxide, triphenylphosphine sulfide, triphenyldichlorophosphine or triphenyldibromophosphine, can particularly advantageously be converted using the novel process. The phenyl radicals may furthermore carry substituents which are inert under the reaction conditions, e.g. alkyl, alkoxy, dialkylamino or cyano.

Phosphine dihalides which are suitable starting materials of the formula (I) are those in which halogen is iodine, fluorine or, in particular, chlorine or bormine.

Advantageously used hydrocarbons are high boiling mineral oils whose boiling points are higher than the reaction temperature, which is 150°–500° C. In general, low temperatures of from 150° to 400° C. are required for the reduction of dihalogen compounds of the formula I or tertiary phosphine sulfides, whereas the temperature in the case Of tertiary phosphine oxides is in the upper part of the range, in particular from 250° to 450° C. Examples of such hydrocarbons are vacuum gas oil, technical-grade white oil, heavy fuel oil, vacuum residues and other high boiling components produced during the fractionation of oil. It is also possible to use low boiling hydrocarbons, such as light fuel oil, gasoline, naphtha, cyclohexane, $C_4$ cuts or natural gas (cf. Ullmann, Enzyklopädie d. tech. Chemie, 3rd edition, vol. 6, pages 595–760, 1955 and 4th edition, vol. 12, pages 570–573). In this case, however, the reaction has to be carried out under superatmospheric pressure. Crude oils of various origins may also be used.

The hydrocarbons are used, as a rule, in an amount of from 100 to 3000 g, in particular from 300 to 2000 g, per mole of phosphine oxide, phosphine sulfide or phosphine dihalide. The reaction is preferably carried out in the liquid phase, and the major part, if not all, of the hydrocarbon must be present in liquid form. The liquid phase contains carbon, which as a rule is in suspended form and is either present as part of the hydrocarbons or is added to the reaction mixture. In the case of heavy fuel oil or vacuum residues, for example, it is not necessary to add carbon since both of these contain a substantial amount of carbon black. The addition of carbon can also be dispensed with when dihalides are reacted, since carbon is formed immediately at the beginning of the reaction.

Examples of carbon additives which are suitable for the reaction are carbon black and petroleum coke. Active carbons are particularly advantageously used. The carbon is preferably present in the reaction mixture in an amount of from 1 to 50, in particular from 5 to 20, % by weight, based on the hydrocarbon. The reaction is carried out continuously or batchwise by a conventional technique, under superatmospheric or reduced pressure but in particular under atomospheric pressure.

The reaction is advantageously carried out as follows: a suspension of carbon in the hydrocarbon is initially taken, and the tertiary phosphorus compound of the general formula I which is to be reduced, in solid, liquid or gaseous form, is fed, if necessary with an inert gas, e.g. nitrogen, to the reactor containing the liquid hydrocarbon phase heated to the reaction temperature. During the reaction, it is advantageous if an inert gas is passed through the reaction mixture and the resulting water of reaction or the hydrogen halide or hydrogen sulfide is removed continuously, for example by distillation. The reaction product is isolated from the mixture by a conventional method, depending on the boiling point of the tertiary phosphine, for example by distillation or extraction.

Surprisingly, the novel process makes it possible to reduce tertiary phosphine oxides directly to the corresponding phosphines in a cheap and technically simple manner, so that the phosphoruse compounds obtained as waste products, for example in the Wittig reaction, can readily by recycled to the process after the reduction.

EXAMPLE 1

250 g of technical-grade white oil and 25 g of powdered active carbon were initially taken in a stirred flask and heated to 350° C. 27.8 g of triphenylphosphine oxide were introduced into this reaction medium, and at the same time a gentle stream of nitrogen (5 l/h of $N_2$) was passed through. The resulting water of reaction was distilled off continuously. After 6 hours, the reaction was complete, and 0.8 g of $H_2O$ had collected in the flask.

The reaction mixture was cooled to room temperature and extracted with 5×100 ml of glacial acetic acid, and the acetic acid was evaporated off to give 28.7 g of crystalline residue which contained 13.3 g of unconverted triphenylphosphine oxide, 9.2 g of triphenylphosphine and acetic acid. The conversion was 52%, with a selectivity of 68%.

EXAMPLE 2

250 g of technical-grade white oil were introduced into a stirred flask, and 33 g (0.1 mole) of triphenylphosphine dichloride were added while flushing with $N_2$. The stirred reaction mixture was heated to 300° C. and kept at this temperature for 5 hours, after which it was heated at 350° C. for a further hour. During the reaction, a stream of about 6 l/h of dry nitrogen was passed through the reaction mixture.

When the mixture was distilled under 0.5 mbar and at a bottom temperature 240° C., 151 g of distillate passed over at 70°–220° C. Analysis of the distillate by gas chromatography indicated the presence of 14.1% by weight of triphenylphosphine and 1.9% by weight of unconverted triphenylphosphine dichloride. This corresponds to a conversion of 91.2% and a selectivity of 89.9%.

I claim:

1. A process for the reduction of teriary phosphine oxides, phosphine sulfides and/or phosphine dihalides to form the corresponding tertiary phosphines, which process comprises:

reacting an organic phosphorus compound of the formula

I where each radical X is halogen or the two radicals X taken together represent an oxo or thio group and R is an aliphatic, cycloaliphatic, araliphatic or aromatic group, with a hydrocarbon in the presence of carbon at a temperature of from 150° to 500° C.

2. A process as claimed in claim 1 wherein tertiary phosphine sulfides and/or phosphine dihalides are reduced at a temperature of from 150° to 400° C.

3. A process as claimed in claim 1 wherein tertiary phosphine oxides are reduced at a temperature of from 250° to 450° C.

4. A process as claimed in claim 1 wherein a high boiling hydrocarbon is used with a boiling point above the reaction temperature.

5. A process as claimed in claim 4 wherein the high boiling hydrocarbon is selected from the group consisting of vacuum gas oil, heavy fuel oil, a vacuum residue and a technical grade white oil.

6. A process as claimed in claim 1 wherein a low boiling hydrocarbon is used under a superatmospheric pressure sufficient to maintain at least the major part of the hydrocarbon in liquid form.

7. A process as claimed in claim 6 wherein the low boiling hydrocarbon is selected from the group consisting of light fuel oil, gasoline, naphtha, cyclohexane, $C_4$ cuts and natural gas.

8. A process as claimed in claim 1 wherein carbon is used in an amount of from 5 to 20% by weight, based on the hydrocarbon.

9. A process as claimed in claim 1 wherein the hydrocarbon is used in an amount of from 100 to 3000 g per mole of the organic phosphorus compound I as the initial reactant.

10. A process as claimed in claim 9 wherein an active carbon is used in an amount of from 1 to 50% by weight, based on the hydrocarbon.

11. A process as claimed in claim 9 wherein an active carbon is used in an amount of from 5 to 20% by weight, based on the hydrocarbon.

12. A process as claimed in claim 1 wherein the hydrocarbon is used in an amount of from 300 to 2000 g per mole of the organic phosphorus compound I as the initial reactant.

13. A process as claimed in claim 12 wherein an active carbon is used in an amount of from 1 to 50% by weight, based on the hydrocarbon.

14. A process as claimed in claim 12 wherein an active carbon is used in an amount of from 5 to 20% by weight, based on the hydrocarbon.

15. A process as claimed in claim 1 wherein an inert gas is passed through a suspension of carbon in the hydrocarbon which forms a liquid reaction medium.

16. A proces as claimed in claim 1, wherein the reaction is carried out in the presence of active carbon, carbon black or petroleum coke.

17. A process as claimed in claim 1, wherein carbon is used in an amount of from 1 to 50% by weight, based on the hydrocarbon.

18. A process as claimed in claim 1, wherein the reaction is carried out in a liquid hydrocarbon.

* * * * *